(12) United States Patent
Stark et al.

(10) Patent No.: US 6,949,747 B2
(45) Date of Patent: Sep. 27, 2005

(54) APPARATUS AND METHOD FOR AUTOMATICALLY ADJUSTING THE PATH OF A MEDICAL CAMERA

(75) Inventors: Iain Stark, Manotick (CA); Zoltan Schreck, Ville de Lery (CA)

(73) Assignee: IS2 Medical Systems Inc., Nepean (CA)

( * ) Notice: Subject to any disclaimer, the term of this patent is extended or adjusted under 35 U.S.C. 154(b) by 129 days.

(21) Appl. No.: 10/140,919

(22) Filed: May 7, 2002

(65) Prior Publication Data

US 2005/0145798 A1    Jul. 7, 2005

Related U.S. Application Data

(63) Continuation-in-part of application No. 09/586,298, filed on Jun. 2, 2000, now abandoned.

(51) Int. Cl.[7] .................................................. G01T 1/20
(52) U.S. Cl. ................................. 250/363.08; 250/366
(58) Field of Search ..................... 250/363.08, 363.02, 250/363.04, 363.05, 366, 367; 378/8, 19, 378/20, 95

(56) References Cited

U.S. PATENT DOCUMENTS

| | | | | |
|---|---|---|---|---|
| 3,899,675 A | * | 8/1975 | Floyd | 250/369 |
| 4,020,348 A | * | 4/1977 | Turcotte et al. | 250/363.08 |
| 4,401,890 A | | 8/1983 | Blum | |
| 4,417,143 A | * | 11/1983 | Haas et al. | 250/363.05 |
| 4,593,189 A | * | 6/1986 | Stoub | 250/221 |
| 4,652,758 A | * | 3/1987 | Barfod | 250/363.04 |
| 4,692,624 A | * | 9/1987 | Ichihara | 250/363.04 |
| 4,888,486 A | | 12/1989 | Plummer et al. | |
| 5,072,121 A | * | 12/1991 | Jazbec | 250/363.04 |
| 6,044,504 A | * | 4/2000 | Stark | 5/601 |

* cited by examiner

*Primary Examiner*—Otilia Gabor
(74) *Attorney, Agent, or Firm*—Pearne & Gordon LLP

(57) ABSTRACT

An apparatus for controlling a relative distance between a patient's body and a camera head in a medical imaging system is disclosed. The apparatus comprises (a) a light source provided at one side of a field of view, which is defined by a camera surface of the camera head, and (b) a light detector provided at the other side of the field of view. The light detector is adapted to detect a light beam emitted by the light source. The apparatus includes means for adjusting a relative distance between the patient's body and the camera surface by sensing an interruption or disturbance in the light beam caused by the patient's body approaching the camera surface to take a picture. A method of controlling a relative distance between a patient's body and a camera head in a medical imaging system is also disclosed.

54 Claims, 15 Drawing Sheets

APPARATUS AND METHOD FOR AUTOMATICALLY ADJUSTING THE PATH OF A MEDICAL CAMERA

This patent application is a continuation-in-part of U.S. patent application Ser. No. 09/586,298 filed on Jun. 2, 2000, now abandoned.

FIELD OF THE INVENTION

The present invention relates to an apparatus and method for automatically adjusting a relative distance between a patient body and a camera head in a medical imaging system.

BACKGROUND OF THE INVENTION

In the human body, increased metabolic activity is associated with an increase in emitted radiation. In the field of nuclear medicine, increased metabolic activity within a patient is detected using a radiation detector such as a scintillation camera.

Scintillation cameras are well known in the art, and are used for medical diagnostics. A patient ingests, or inhales or is injected with a small quantity of a radioactive isotope. The radioactive isotope emits photons that are detected by a scintillation medium in the scintillation camera. The scintillation medium is commonly a sodium iodide crystal, BGO or other. The scintillation medium emits a small flash or scintillation of light, in response to stimulating radiation, such as from a patient. The intensity of the scintillation of light is proportional to the energy of the stimulating photon, such as a gamma photon. Note that the relationship between the intensity of the scintillation of light and the gamma photon is not linear.

A conventional scintillation camera such as a gamma camera includes a detector which converts into electrical signals gamma rays emitted from a patient after radioisotope has been administered to the patient. The detector includes a scintillator and photomultiplier tubes. The gamma rays are directed to the scintillator which absorbs the radiation and produces, in response, a very small flash of light. An array of photodetectors, which are placed in optical communication with the scintillation crystal, converts these flashes into electrical signals which are subsequently processed. The processing enables the camera to produce an image of the distribution of the radioisotope within the patient.

Gamma radiation is emitted in all directions and it is necessary to collimate the radiation before the radiation impinges on the crystal scintillator. This is accomplished by a collimator which is a sheet of absorbing material, usually lead, perforated by relatively narrow channels. The collimator is detachably secured to the camera head, allowing the collimator to be changed to enable the camera head to be used with the different energies of isotope to suit particular characteristics of the patient study. A collimator may vary considerably in weight to match the isotope or study type.

Scintillation cameras are used to take four basic types of pictures: spot views, whole body views, partial whole body views, SPECT views, and whole body SPECT views.

A spot view is an image of a part of a patient. The area of the spot view is less than or equal to the size of the field of view of the gamma camera. In order to be able to achieve a full range of spot views, a gamma camera must be positionable at any location relative to a patient.

One type of whole body view is a series of spot views fitted together such that the whole body of the patient may be viewed at one time. Another type of whole body view is a continuous scan of the whole body of the patient. A partial whole body view is simply a whole body view that covers only part of the body of the patient. In order to be able to achieve a whole body view, a gamma camera must be positionable at any location relative to a patient in an automated sequence of views.

The acronym "SPECT" stands for single photon emission computerized tomography. A SPECT view is a series of slice-like images of the patient. The slice-like images are often, but not necessarily, transversely oriented with respect to the patient. Each slice-like image is made up of multiple views taken at different angles around the patient, the data from the various views being combined to form the slice-like image. In order to be able to achieve a SPECT view, a scintillation camera must be rotatable around a patient, with the direction of the camera head of the scintillation camera pointing in a series of known and precise directions such that reprojection of the data can be accurately undertaken.

A whole body SPECT view is a series of parallel slice-like transverse images of a patient. Typically, a whole body SPECT view consists of sixty four spaced apart SPECT views. A whole body SPECT view results from the simultaneous generation of whole body and SPECT image data. In order to be able to achieve a whole body SPECT view, a scintillation camera must be rotatable around a patient, with the direction of the camera head of the scintillation camera pointing in a series of known and precise directions such that reprojection of the data can be accurately undertaken.

Therefore, in order that the radiation detector be capable of achieving the above four basic views, the support structure for the radiation detector must be capable of positioning the radiation detector in any position relative to the patient. Furthermore, the support structure must be capable of moving the radiation detector relative to the patient in a controlled manner along any path.

In order to operate a scintillation camera as described above, the patient should be supported horizontally on a patient support or stretcher.

The camera head must also be positioned at a certain height relative to the patient. It is commonly known in the art that when the collimator to patient distance is minimized, the better the image resolution develops. However, many patients do not feel comfortable with the camera head too close to them. An optimum position must be maintained to ensure a good quality view and patient comfort.

It is therefore necessary to provide an apparatus for and a method of automatically adjusting a relative distance between a camera head and a patient in a medical imaging system.

SUMMARY OF THE INVENTION

According to one aspect of the present invention, there is provided an apparatus for controlling a relative distance between a patient's body and a camera head in a medical imaging system, in which the camera head has a camera surface defining a field of view where the patient's body is to be placed. The apparatus comprises: (a) a light source provided at one side of the field of view, the light source being adapted to emit a light beam which travels over and substantially parallel to the camera surface; (b) a light detector provided at the other side of the field of view, the light detector being adapted to detect said light beam emitted from said light source; (c) wherein, when in use, the camera head approaches the patient's body or vice versa to take a picture and an interruption or disturbance in the light beam by said approaching patient's body is sensed by the light detector; and (d) means for adjusting a relative distance between the patient's body and the camera surface according to the characteristics of the interruption or disturbance sensed by the light detector.

According to another aspect of the invention, there is provided an apparatus for adjusting a relative distance between a patient's body and a camera head in a medical imaging system, in which the camera head has a camera surface defining a field of view where the patient's body is to be placed. The apparatus comprises: (a) a light source provided at one side of the field of view, said light source being adapted to emit a light beam in such a manner that the light beam can sweep substantially the whole area of the camera surface; (b) a light detector provided at the other side of the field of view, the light detector being adapted to detect the sweeping light beam at multiple heights over the camera surface; (c) wherein, when in use, the light beam is partially interrupted by a patient's body placed in the field of view: and (d) means for adjusting the relative distance between the camera surface and the patient's body according to the characteristics of the detected light beam, whereby the camera surface can be maintained at a predetermined distance from the patient's body.

According to yet another aspect of the invention, there is provided a method of controlling a relative distance between a patient's body and a camera head in a medical imaging system, in which the camera head has a camera surface defining a field of view where the patient's body is to be placed. The method comprises steps of: (a) projecting a light beam from one side of the field of view in such a manner that the light beam travels over and substantially parallel to the camera surface; (b) detecting the light beam at the other side of the field of view, wherein the light beam is interrupted by the patient placed in the filed of view; (c) analysing the interrupted characteristics in the detected light beam; and (d) adjusting the relative distance between the camera surface and the patient's body according to the analysed result, whereby the camera surface can be maintained at a predetermined distance from the patient's body.

A further understanding of other advantages, objects and features of the present invention will be realized by reference to the following description, appended claims, and accompanying drawings.

BRIEF DESCRIPTION OF THE DRAWINGS

The embodiments of the invention will now be described with reference to the accompanying drawings, in which.

DETAILED DESCRIPTION OF THE PREFERRED EMBODIMENT(S)

Figure 1:
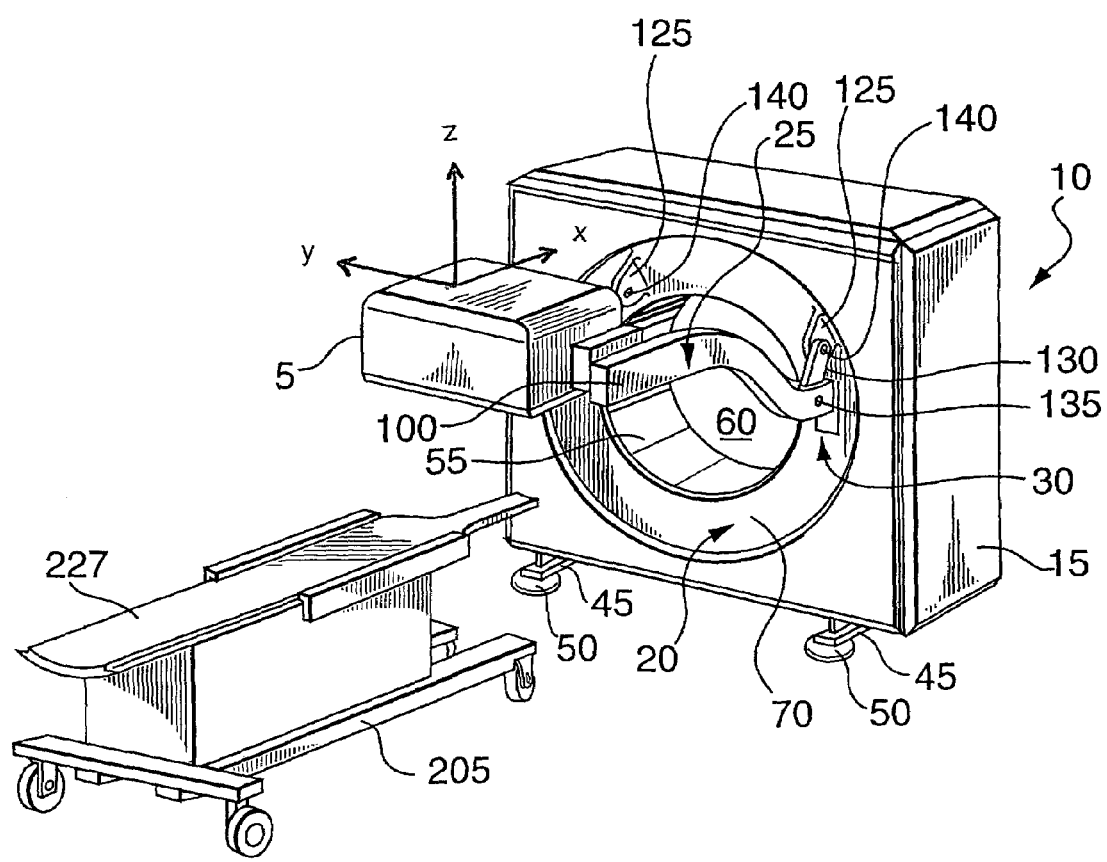
FIG. 1 is a perspective view of a scintillation camera including a detached patient support in accordance with the invention.
Figure 2:
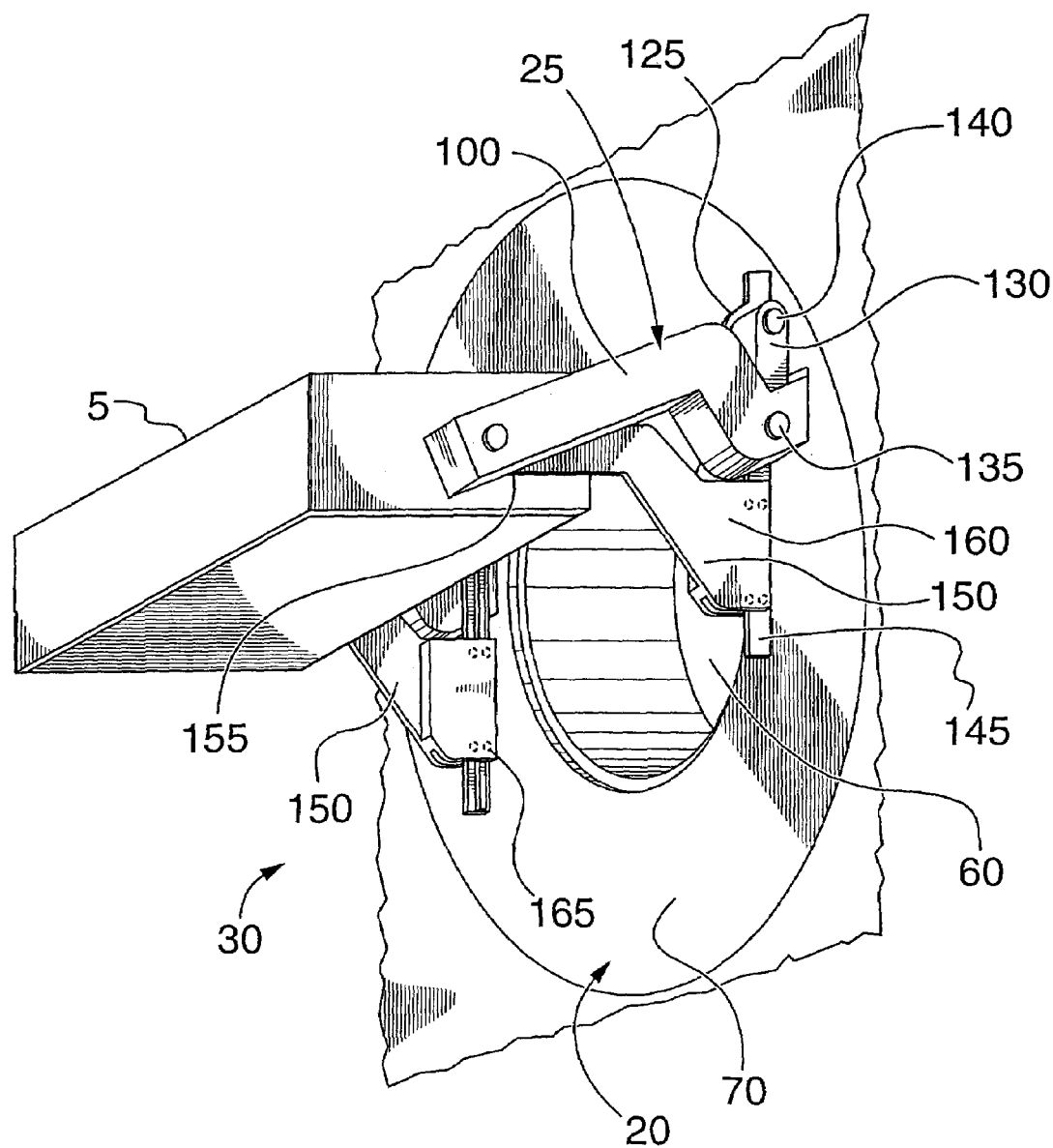
FIG. 2 is a perspective view of the guide of a scintillation camera.
Figure 3:
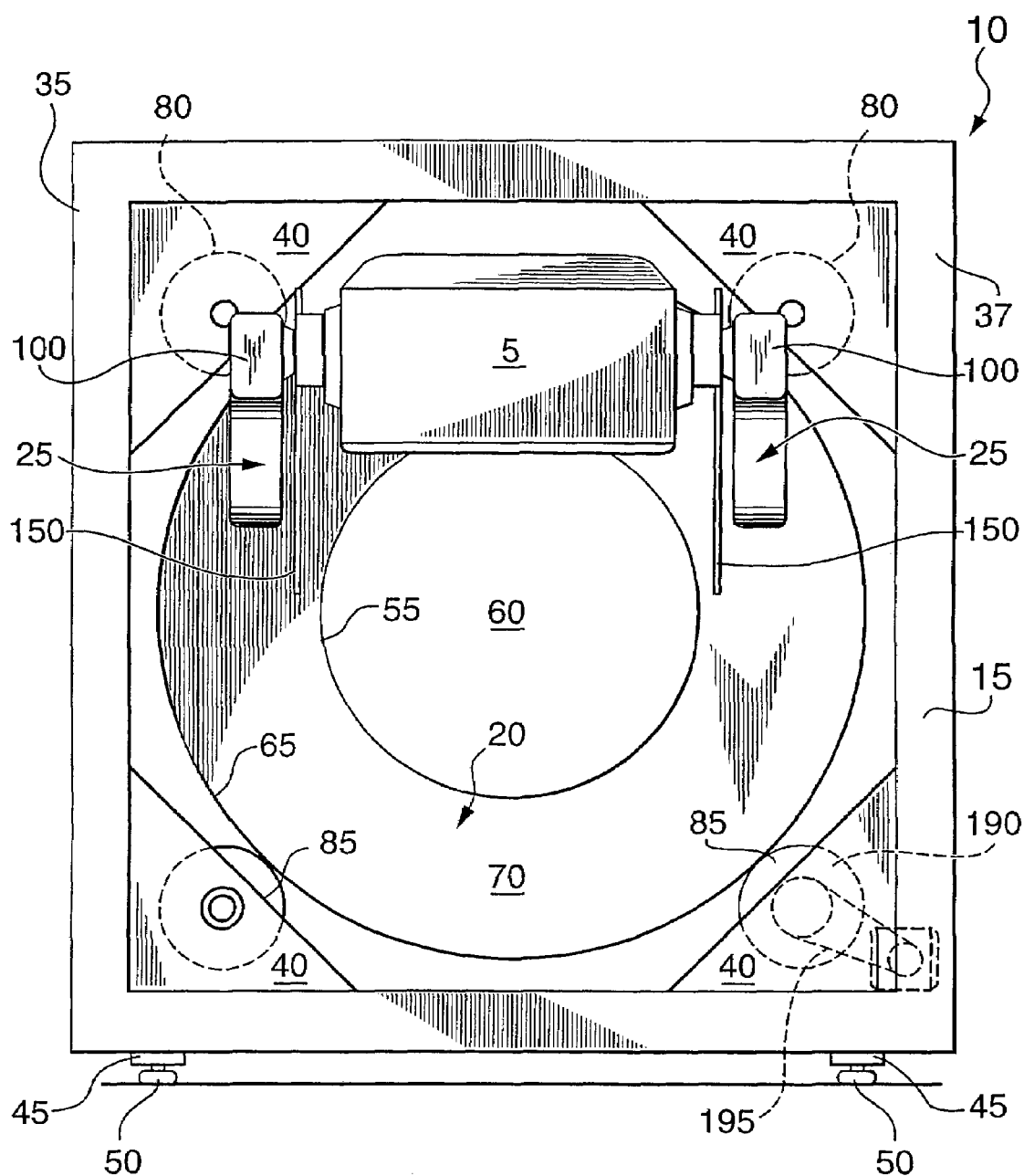
FIG. 3 is a front elevation view of a scintillation camera.
Figure 4:
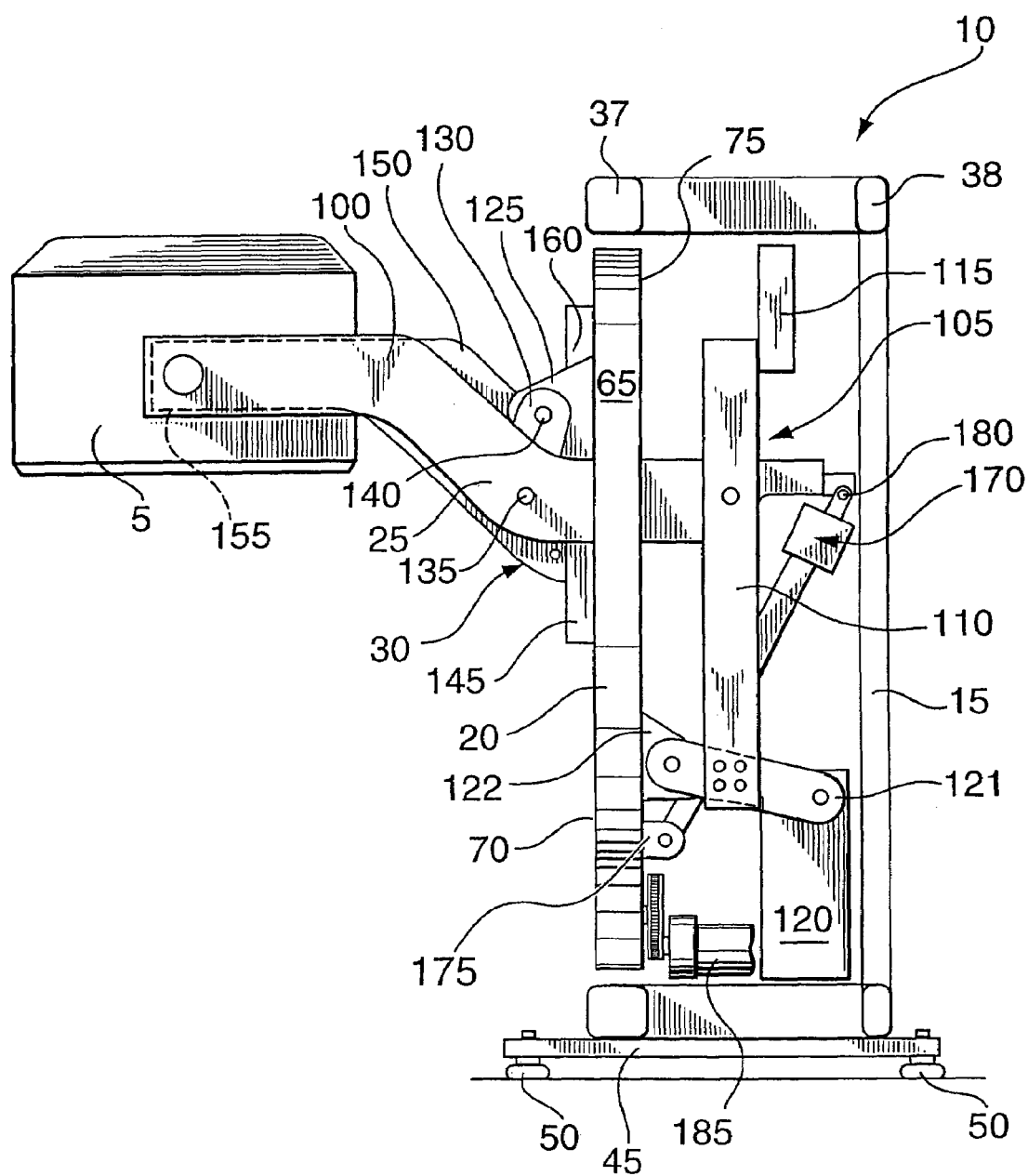
FIG. 4 is a side elevation view of a scintillation camera.
Figure 5:
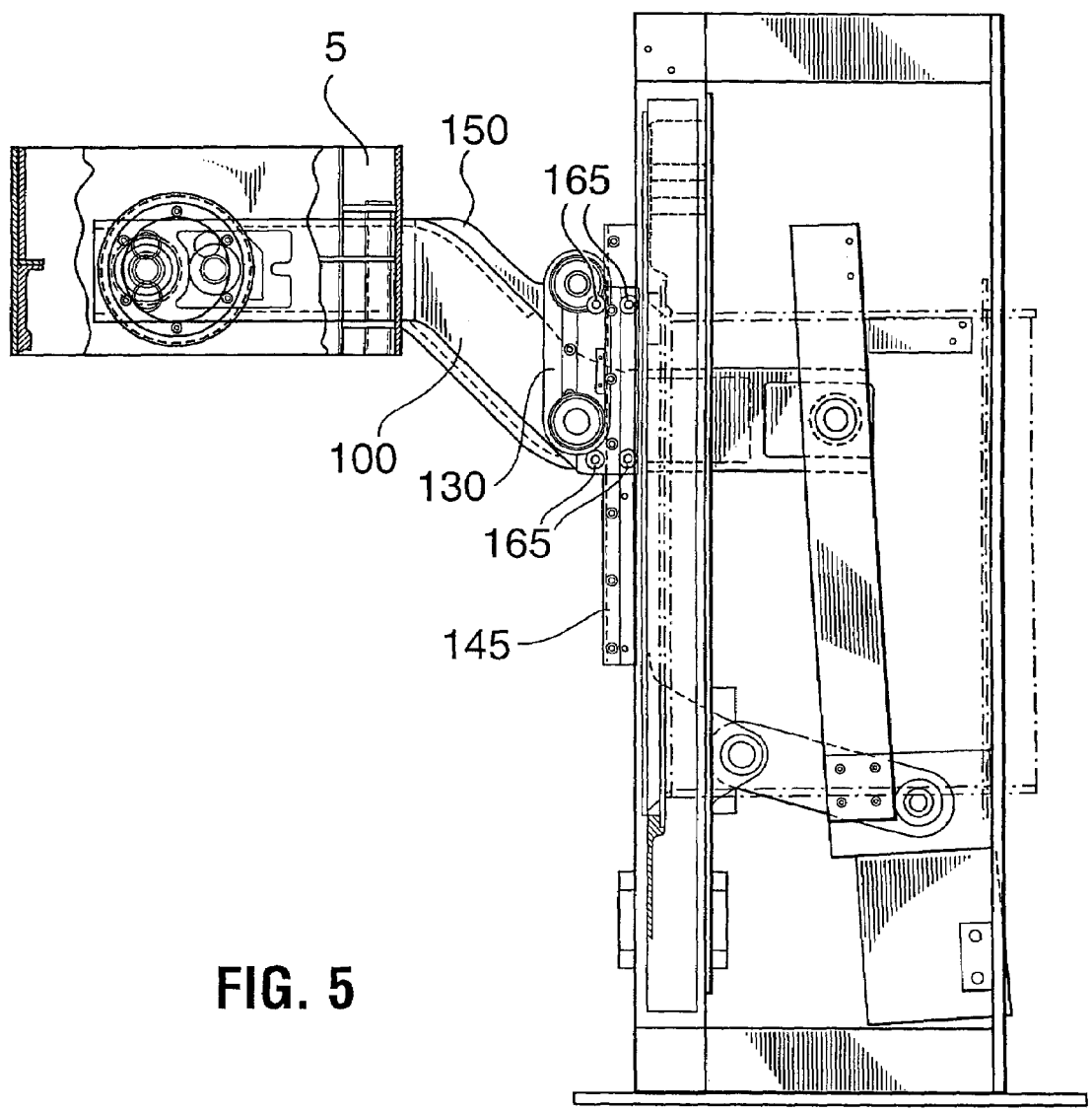
FIG. 5 is a side elevation view of a scintillation camera.
Figure 6:
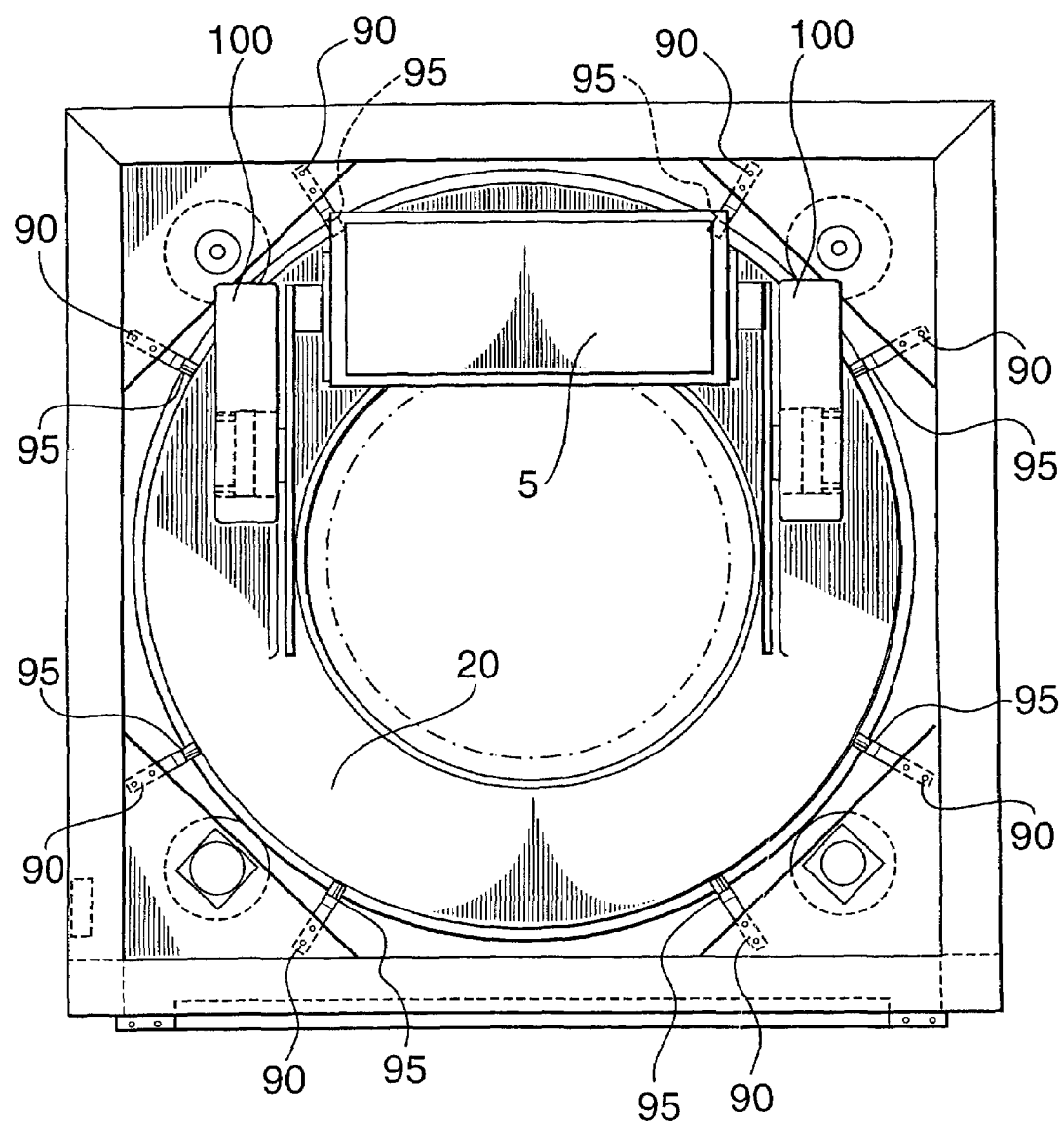
FIG. 6 is a front elevation view of a scintillation camera.
Figure 7:
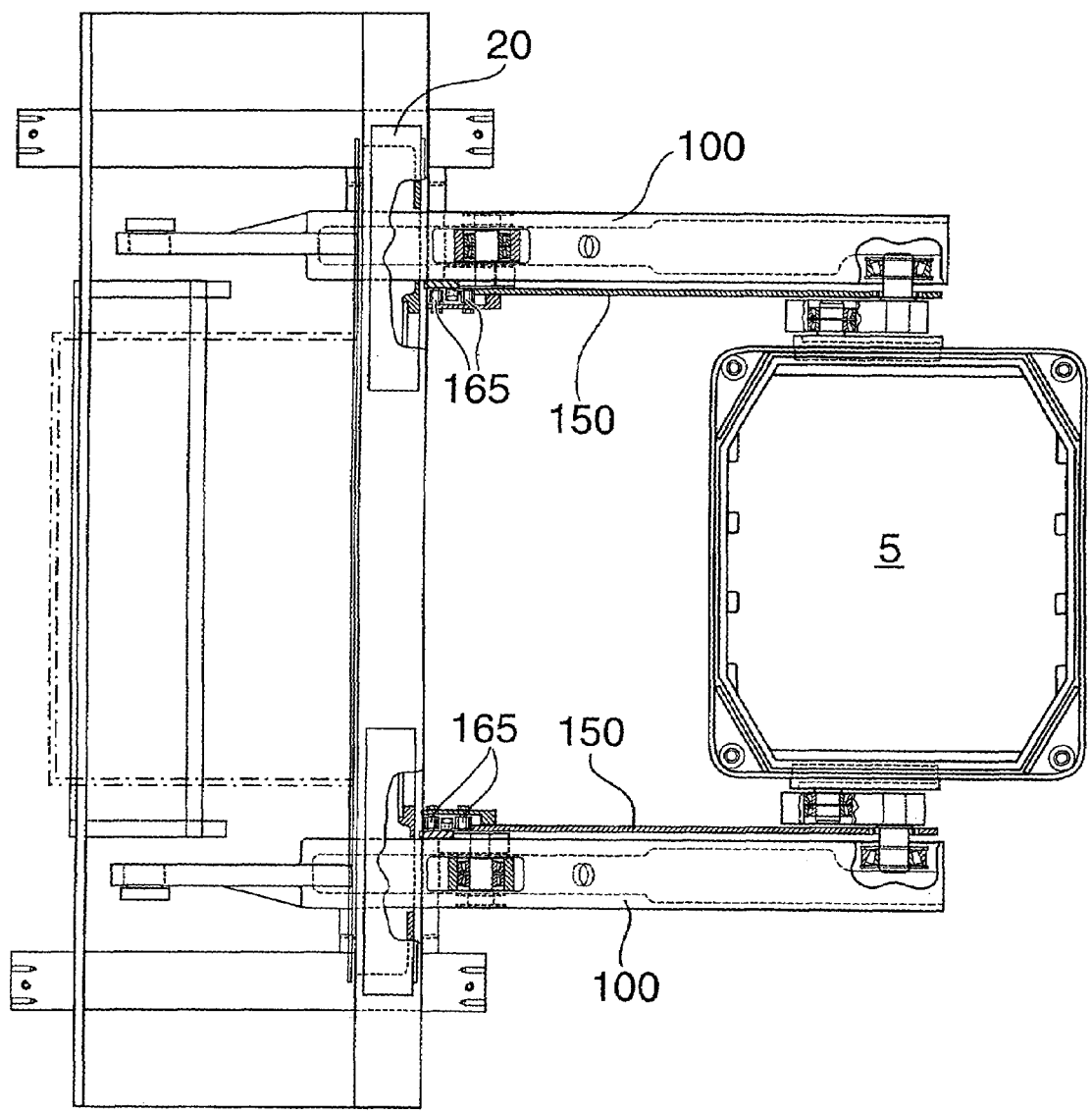
FIG. 7 is a top plan view of a scintillation camera.

Before describing the preferred embodiment(s) of the present invention, a general configuration and operation of a scintillation camera will be detailed, where the present invention can be applied. However, it is to be noted that the invention can be used in any medical camera environment.

Referring to FIGS. 1 to 12, a scintillation camera 5 is supported and positioned relative to a patient by a support structure 10. Nuclear cameras are heavy, usually weighing approximately three to four thousand pounds. Thus, the support structure 10 should be strong and stable in order to be able to position the camera 5 safely and accurately. The support structure 10 includes a base 15, an annular support 20, an elongate support 25, and a guide 30.

The base 15 includes a frame 35. The frame 35 includes twelve lengths of square steel tubing welded together in the shape of a rectangular parallelepiped. The frame 35 has a front square section 37 and a rear square section 38. The frame 35 is approximately five feet wide, five feet high, and two feet deep. The frame 35 also includes eight triangular corner braces 40 welded to the front square section 37, that is, each corner of the front square section 37 has two corner braces 40, one towards the front of the front square section 37, and one towards the rear of the front square section 37. The corner braces 40 are in the shape of equilateral right angle triangles.

Attached to the underside of the frame 35 are two horizontal legs 45. Attached to each leg 45 are two feet 50. An alternative to the use of feet 50 is to attach the base 15 to a floor by way of bolts set into the floor. The legs 45 extend beyond the frame 35 so as to position the feet 50 wider apart to increase the stability of the base 15. The feet 50 are adjustable so that the base 15 may be levelled. Thus constructed, the base 15 is strong, stable, rigid, and capable of supporting heavy loads.

The annular support 20 is vertically oriented, having an inner surface 55 defining an orifice 60, an outer surface 65, a front surface 70, and a rear surface 75. The annular support 20 is constructed of a ductile iron casting capable of supporting heavy loads. The annular support 20 has an outside diameter of about fifty two inches (about 132 centimeters). The annular support 20 is supported by upper rollers 80 and lower rollers 85 which are mounted on the base 15. The upper rollers 80 and lower rollers 85 roll on the outer surface 65, thus enabling the annular support 20 to rotate relative to the base 15 in the plane defined by the annular support 20. Each of the upper rollers 80 and lower rollers 85 are mounted onto a pair of corner braces 40 by way of axles with deep groove bearings. The bearings should be low friction and be able to withstand heavy loads. The axles of the upper rollers 80 are radially adjustable relative to the annular support 20, so that the normal force exerted by the upper rollers 80 on the outer surface 65 is adjustable. The curved surfaces of the upper rollers 80 and lower rollers 85 (i.e. the surfaces that contact the outer surface 65) should be tough so as to be able to withstand the pressures exerted by the annular support 20, and should have a fairly high coefficient of friction so as to roll consistently relative to the annular support 20.

Attached to each pair of corner braces 40 is a stabilizing arm (not shown) oriented perpendicularly to the plane of the annular support 20. A pair of small stabilizing rollers are mounted (not shown) onto each stabilizing arm. Each pair of stabilizing rollers is positioned such that one stabilizing roller rolls on the front surface 70, and the other stabilizing roller rolls on the rear surface 75. The stabilizing rollers maintain the annular support 20 in the vertical plane.

The elongate support 25 includes a pair of support arms 100, each of which extends through an aperture in the annular support 20. The nuclear camera 5 is rotatably attached to one end of the pair of support arms 100, such that the nuclear camera 5 faces the front surface 70. A counter weight 105 is attached to the other end of the pair of support arms 100, such that the counterweight 105 faces the rear surface 75.

The counter weight 105 includes a pair of parallel counter weight members 110, each of which is pivotally attached to one of the support arms 100. A first weight 115 is attached to one end of the pair of counterweight members 110, and a second weight 120 is attached to the other end of the pair of counter weight members 110. A pair of counter weight links 121 connect the counter weight members 110 to the annular support 20. Each counter weight link 121 is pivotally attached at one end to its corresponding counterweight member 110. Each counter weight link 121 is pivotally attached at its other end to a counterweight bracket 122 which is rigidly attached to the annular support 20. The counter weight links 121 are attached to the counterweight members 110 and counter weight brackets 122 using bolts and tapered roller bearings. Each counterweight link 121 is pivotable relative to the annular support 20 in a plane perpendicular to and fixed relative to the annular support 20.

The guide 30 attaches the elongate support 25 to the annular support 20, and controls the position of the elongate support 25, and hence the scintillation camera 5, relative to the annular support 20. A pair of brackets 125 is rigidly attached to the annular support 20. A pair of rigid links 130 is pivotally attached at support arm pivot points 135 to the support arms 100. The pair of links 130 is also pivotally attached at bracket pivot points 140 to the brackets 125. At the support arm pivot points 135 and bracket pivot points 140 are tapered roller bearings mounted with bolts. Each link 130 is pivotable relative to the annular support 20 in a plane perpendicular to and fixed relative to the annular support 20. Thus, as the annular support 20 rotates relative to the base 15, the respective planes in which each link 130 and each support arm 100 can move remain fixed relative to the annular support 20.

A pair of linear tracks 145 are rigidly attached to the front surface 70 of the annular support 20. The tracks 145 are oriented such that they are parallel to the respective planes in which each link 130 and each support arm 100 can move. A pair of rigid sliding arms 150 (not shown in FIG. 1) include camera ends 155 and straight ends 160. Each camera end 155 is pivotally attached to one of the support arms 100 at the point of attachment of the scintillation camera 5. Each straight end 160 includes a pair of spaced apart cam followers or guides 165 slidable within the corresponding track 145. Thus, movement of the scintillation camera 5 relative to the annular support 20 (i.e. we are not concerned, at this point, with rotational movement of the scintillation camera 5 relative to the elongate support 25) is linear and parallel to the plane of the annular support 20. Note that if the camera ends 155 were pivotally attached to the support arms 100 between the nuclear camera 5 and the annular support 20, the movement of the nuclear camera 5 relative to the annular support 20 would not be linear.

Movement of the scintillation camera 5 relative to the annular support 20 is effected by an actuator 170. The actuator 170 includes a fixed end 175 pivotally attached to the annular support 20, and a movable end 180 pivotally attached to the elongate support 25. The actuator 170 is extendable and retractable, and is thus able to move the elongate support 25 relative to the annular support 20.

Movement of the annular support 20 relative to the base 15 is effected by a drive unit 185. The drive unit 185 includes a quarter horsepower permanent magnet DC motor and a gearbox to reduce the speed of the output shaft of the drive unit 185. Alternatively, other types of motors could be used, such as hydraulic or pneumatic motors. The output shaft of the drive unit 185 is coupled, by means of a toothed timing belt 195 and two pulley wheels 200, to the axle of a drive roller 190, which is simply one of the lower rollers 85, thus driving the drive roller 190. Power is then transferred from the drive roller 190 to the annular support 20 by friction between the drive roller 190 and the outer surface 65 of the annular support 20.

The support structure 10 is designed to operate with an apparatus for supporting and positioning a patient, such apparatus including a detached patient support 205, an engaged patient support 210, and a cylinder 245.

The detached patient support 205 includes rigid patient frame 215 supported by four casters 220. Mounted near the top of the patient frame 215 are first support wheels 225 for supporting a stretcher 227 upon which a patient is lying. Two parallel, spaced apart side rails 230 are rigidly attached to the patient frame 215. The first support wheels 225 and the side rails 230 are arranged to enable the stretcher 227 to roll lengthwise on the detached patient support 205. Thus, if the patient support 205 faces the front surface 70 such that the patient support is central and perpendicular relative to the annular support 20, the stretcher 227 is movable on the first patient support wheels 225 substantially along the axis of the annular support 20. A gear box and motor unit 237 driving at least one of the first patient support wheels 225 moves the stretcher 227 as described. A 0.125 horsepower permanent magnet DC motor has been found to be adequate.

The detached patient support 205 can be used both for transporting a patient to and from the scintillation camera 5 and support structure 10 therefor, and for supporting and positioning a patient relative to the base 15 during operation of the scintillation camera 5 and support structure 10. To ensure that the detached patient support 205 remains stationary during operation of the scintillation camera 5, four stabilizers 233 can be lowered. Thus lowered, the stabilizers 233 ensure that the detached patient support remains stationary relative to the floor.

The engaged patient support 210 includes second support wheels 235. The second support wheels 235 are positioned such that the stretcher 227 rolled along the first support wheels 225 can roll onto the second support wheels 235 until the stretcher 227 is either fully or partially supported by the second support wheels 235. The engaged patient support 210 also includes four transverse wheels 240.

The cylinder 245 is rigidly mounted to the annular support 20. The cylinder 245 is aligned with the orifice 60 of the annular support 20 such that the cylinder is coaxial with the annular support 20. The cylinder 245 includes a smooth inner surface 246 upon which rest the transverse wheels 240 of the engaged patient support 210. Thus, the arrangement is such that the patient remains stationary substantially along the axis of the annular support 20 as the annular support 20 rotates relative to the base 15, regardless of whether the board or stretcher is supported by the first support wheels 225, the second support wheels 235, or both.

The engaged patient support 210 also includes a stabilizer 250. The stabilizer 250 includes outside wheels 255 to maintain the engaged patient support 210 horizontal, that is, to stop the engaged patient support from tipping relative to the cylinder 245. The outside wheels 255 roll on the outside surface 243 of the cylinder 250. The stabilizer 245 also includes end wheels 256 to prevent the engaged patient support 210 from moving in a direction parallel to the axis of the cylinder 215. The end wheels 256 roll on the ends 244 of the cylinder 245.

Figure 10:
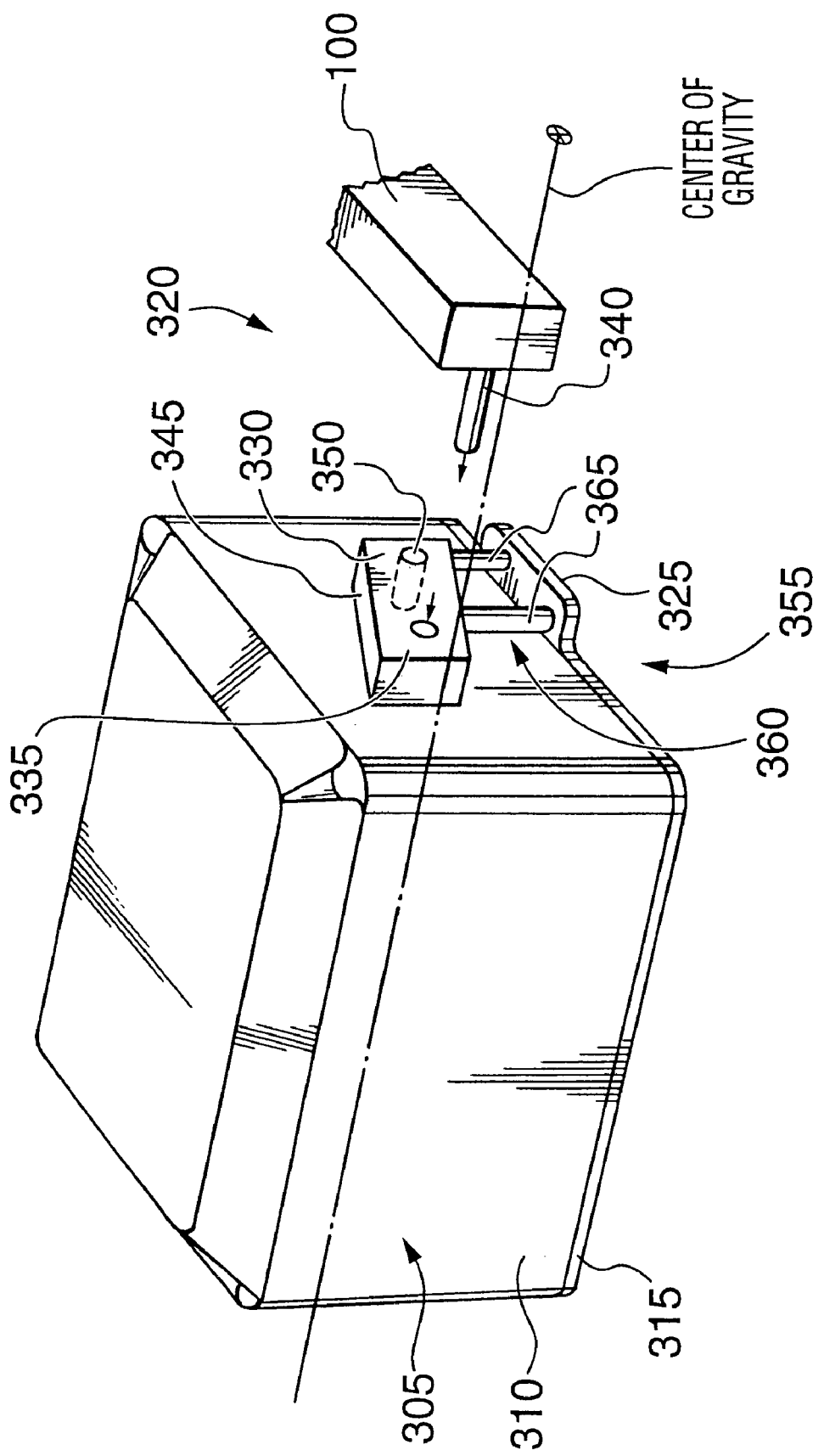
FIG. 10 is a perspective view of the positioner.
Figure 11:
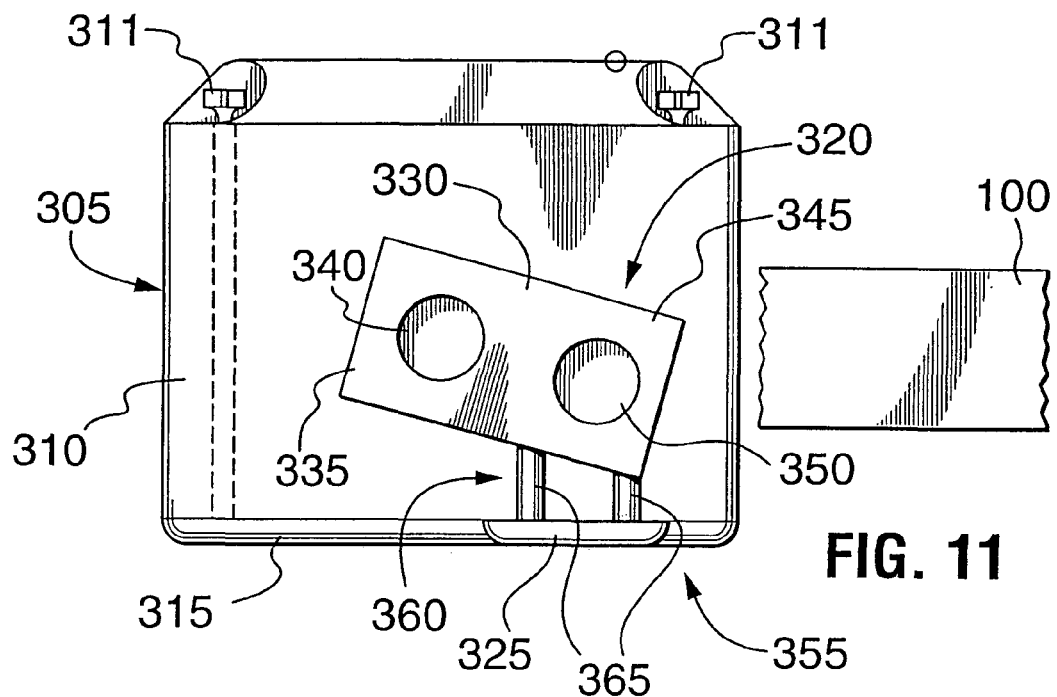
FIG. 11 is a side elevation view of the positioner.
Figure 12:
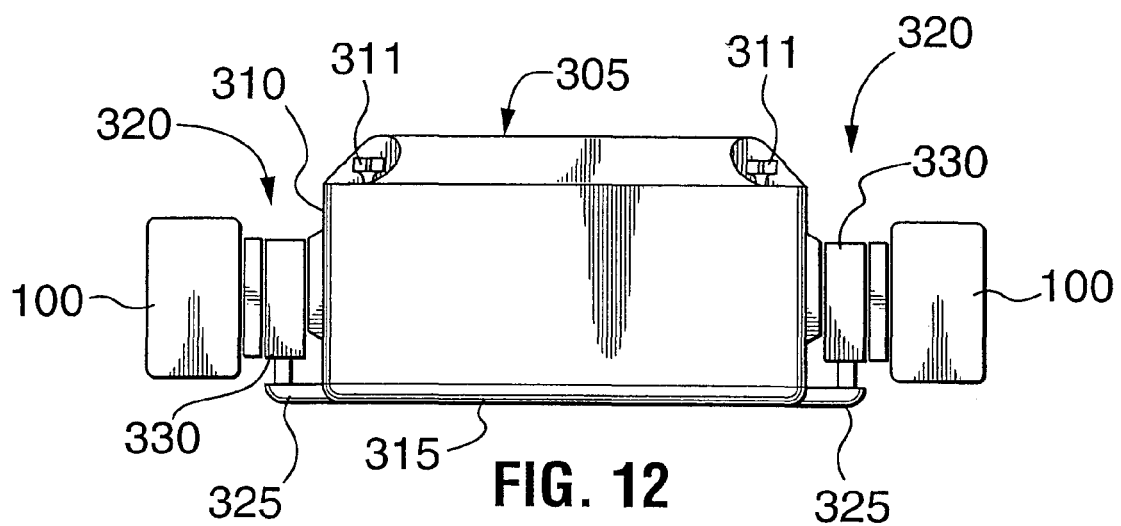
FIG. 12 is a front elevation view of the positioner.

Referring to FIGS. 10, 11 and 12, a camera head 305 of the nuclear camera 5 is supported between the two support arms 100 by a positioner 320. The camera head 305 includes a casing 310 in which is contained a scintillation crystal and photomultiplier tubes. Attached to the underside of the casing 310 is a collimator plate 315. The collimator plate 315 is made of lead perforated by narrow channels, and includes a collimator support 325 extending from the two edges of the collimator plate adjacent the support arms 100. The collimator plate 315 is attached to the casing 310 by way of bolts 311. By removing the bolts 311, the collimator plate 315 can be removed from the casing 310 and replaced by another collimator plate 315. A particular design and weight of collimator is selected depending on the isotope being used or the type of study being conducted. Thus, the collimator plate 315 must be changed from time to time. Since the collimator plates 315 vary considerably in weight from one to another, the location of centre of gravity of the camera head 305 is dependent upon the weight of the collimator plate 315 attached to the casing 310. Since the angle of the camera head 305 relative to the patient must be adjusted by an operator of the nuclear camera 5, the camera head 305 must be rotatable relative to the arms 100. If the centre of gravity of the camera head 305 is positioned approximately on the axis of rotation of the camera head relative to the support arms 100, then the camera head 305 will be balanced, and the angle of the camera head 305 relative to the support arms 100 will be adjustable by hand. However, changing the collimator plates moves the centre of gravity of the camera head. Since collimator plates 315 are so heavy, it becomes inconvenient or impossible to adjust the angle of the camera head 305 by hand. The positioner 320 enables the operator to adjust the position of the centre of gravity of the camera head 305 to be approximately aligned with the point of rotation of the camera head 305, which passes through the support arms 100.

The positioner 320 attaches the camera head 305 to the support arms 100 and includes a pair of rigid elongate camera head links 330 for aligning the centre of gravity of the camera head 305 relative to the support arms 100. Each camera head link 330 is rotatable relative to the support arms 100 in a plane substantially parallel to its adjacent support arm 100. Each camera head link 330 includes an arm end 335 rotatably attached to the adjacent support arm 100 by way of an arm axle 340. Each camera head link 330 also includes a head end 345 rotatably attached to the camera head 305 by way of a head axle 350.

The positioner 320 also includes a pair of locks 355 for selectively preventing rotation of the camera head 305 relative to the camera head links 330. Each lock 355 includes the collimator support 325 extending 305 from the collimator plate 315. Each lock 355 also includes a block 360 for supporting the camera head link 330 on the collimator support 325. Each block 360 includes a pair of pins 365 located either side of the head axle 350.

In operation, each lock 355 supports the head end 345 of one of the camera head links 330 on the corresponding collimator support 325. Thus, the distance between the head axle 350 and the collimator support 325 remains constant, and rotation of the camera head 305 relative to the camera head link 330 is prevented.

If a heavier collimator plate 315 is installed, shorter pins 365 are installed, thus reducing the distance between the head axle 350 and the collimator support 325, and aligning the centre of gravity of the camera head 305 with the axis of rotation of the camera head 305, which passes through the arm axles 340.

If a lighter collimator plate 315 is installed, longer pins 365 are installed, thus increasing the distance between the head axle 350 and the collimator support 325, and aligning the centre of gravity of the camera head 305 with the axis of rotation of the camera head 305, which passes through the arm axles 340.

Once the locks 355 are in place, the camera head 305 will be balanced, and the camera head 305 can be rotated manually by the operator. Once the camera head 305 has been rotated to the desired position relative to the support arms 100, a brake (not shown) can be implemented to selectively prevent rotation of the camera head link about the arm axle 340.

As previously discussed, the camera head should be positioned at an ideal height relative to the patient's body for producing a clear view while maintaining patient comfort. Thus, the present invention is to provide an apparatus and method for controlling or adjusting a relative distance between the camera head and the patient's body.

Figure 13:
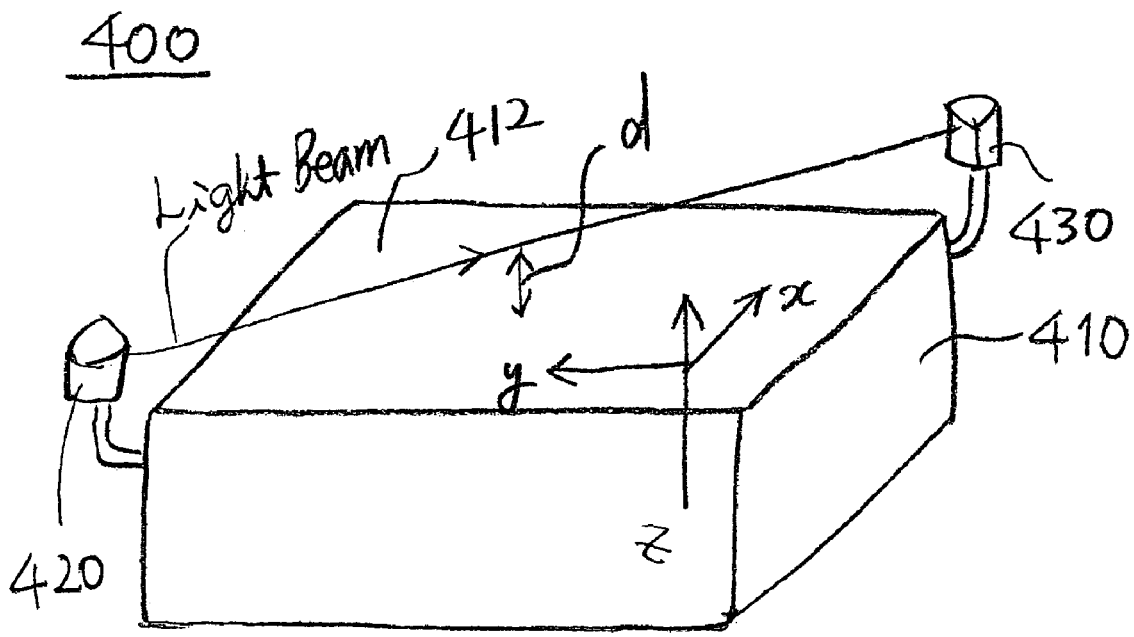
FIG. 13 illustrates a perspective view of an apparatus for controlling a relative distance between a camera head and a patient's body in a medical imaging system according to one embodiment of the invention.
Figure 14:
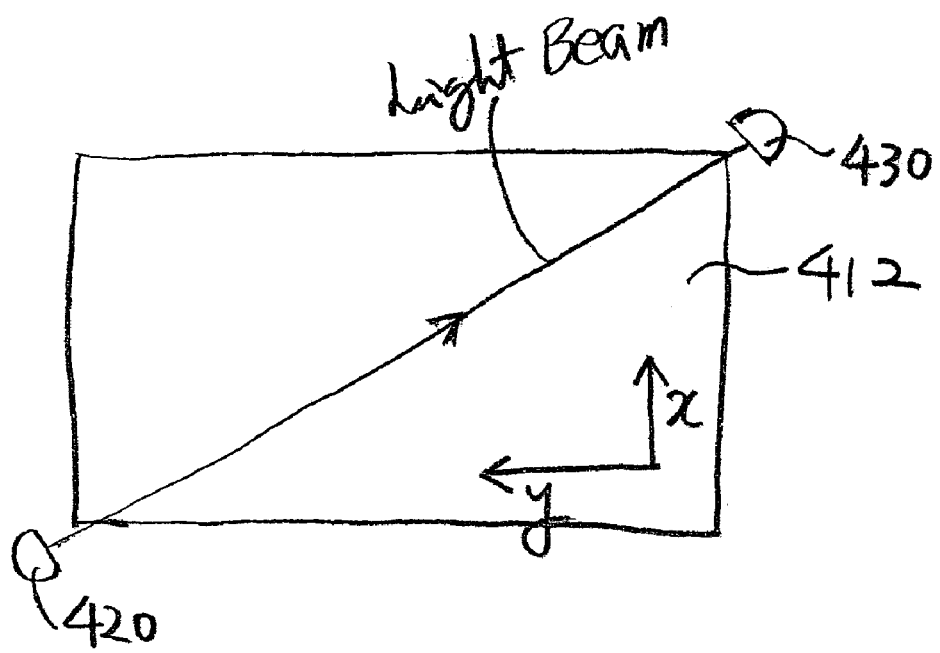
FIG. 14 shows a top view of the apparatus of FIG. 13.

In FIGS. 13 and 14, there is schematically shown an apparatus for controlling a relative distance between a camera head and a patient's body in a scintillation camera system. FIG. 13 is a perspective view of the apparatus and FIG. 14 is a top view thereof. As noted above, the invention can be applied to any medical imaging system which is required to be maintained at a certain distance from a patient's body. As depicted in FIGS. 13 and 14, the apparatus, which is generally denoted by a reference numeral 400, comprises a light source 420 mounted on one side of a camera head 410 and a light detector 430 mounted on the other side of the camera head 410. The camera head 400 includes a camera surface 412, which defines a field of view where the patient's body is to be placed to take a picture. Therefore, the light source 420 is disposed at one side of the field of view, and the light detector 430 at the other side of the field of view of the camera head 410.

The light source 420 and detector 430 are, for example detachably, mounted on the camera head 410 such that the collimator plates thereof can be easily removed and replaced.

Figure 8:
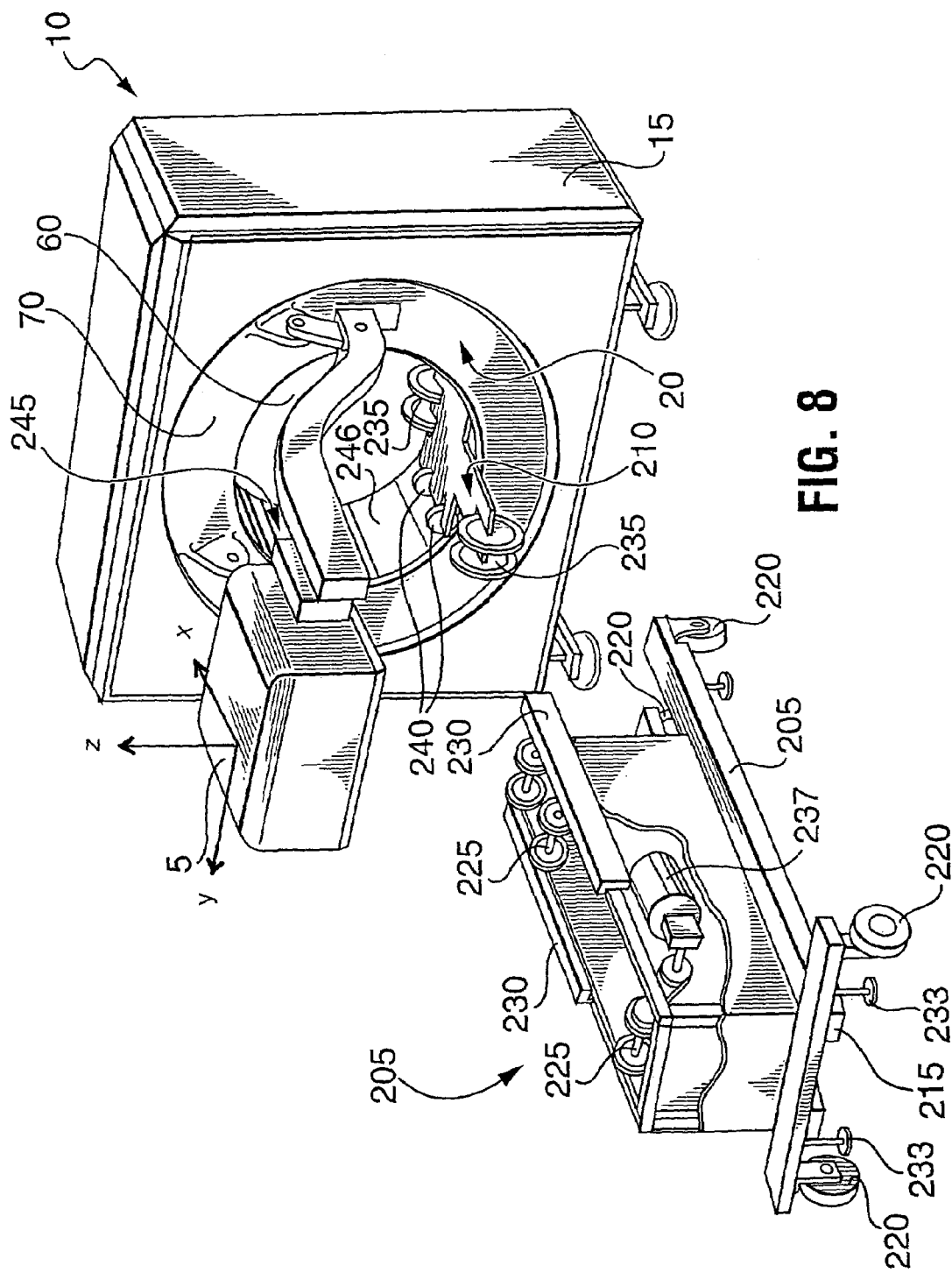
FIG. 8 is a perspective view of the scintillation camera of FIG. 1, including the detached patient support and engaged patient support, with the stretcher removed.
Figure 9:
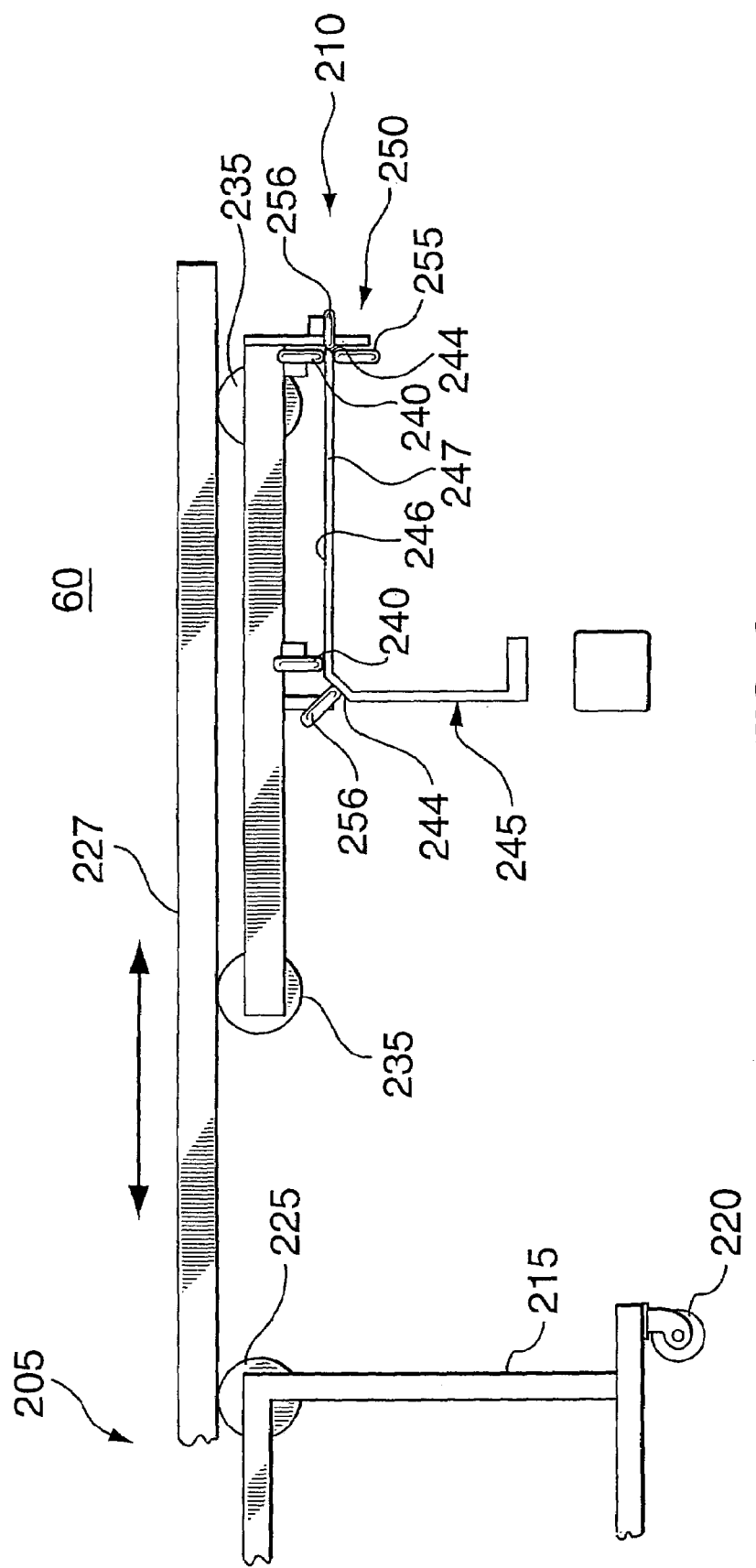
FIG. 9 is a side view of a portion of the patient support apparatus.

For the convenience of description, it will be assumed that the camera head 410 is operated in a rectangular coordinate system. The X and Y-axes lie in the plane of the camera surface 412, while axis Z runs through the camera surface 412. The Z-axis is the axis along which the camera head 410 moves along during adjusting the relative distance between the camera surface 412 and the patient's body, as shown in FIG. 1 or 8.

In operation, the light source 420 emits a light beam, which travels through the field of view defined by the camera surface 412 and substantially parallel to the surface 412. As is shown in FIG. 13, the light beam emitted from the light source 420 travels over the camera surface while maintaining a predetermined distance d from the camera surface 412. The light detector 430 detects the light beam which has travelled across the camera surface 412. Therefore, when a patient's body approaches the camera head (i.e., the camera surface 412) or vice versa to take a picture, the light beam will be interrupted or disturbed by the approaching patient. Then, the interruption or disturbance of the light beam will be sensed by the light detector 430, compared with a normal detection without any interruption or disturbance in the light beam. According to the pattern or characteristics of the disturbance sensed by the light detector 430, the distance between the patient's body and the camera surface 412 can be controlled. For example, in this embodiment, when any interruption or disturbance in the light beam is detected by the light detector 430, the camera head 410 or the patient's body stops further approaching, thereby maintaining the patent's body at the predetermined distance d from the camera surface 412 or vice versa. The distance d can be adjusted, depending on the study.

The light source 420 includes any kind of visible or invisible light emitting devices, as long as the light emitted therefrom is not transmittable through the patient body and can be detected by the light detector 430. For example, the light source may include a laser, which has a good controllability in the beam size, cross-section and width. The light detector 430 also includes any kind of photo-detectors or photo-sensors if they can detect the light beam emitted by the light source and sense any interruption or disturbance in the detected light beam. For example, the light source may include a charge coupled device (CCD) or a photodiode.

Figure 15:
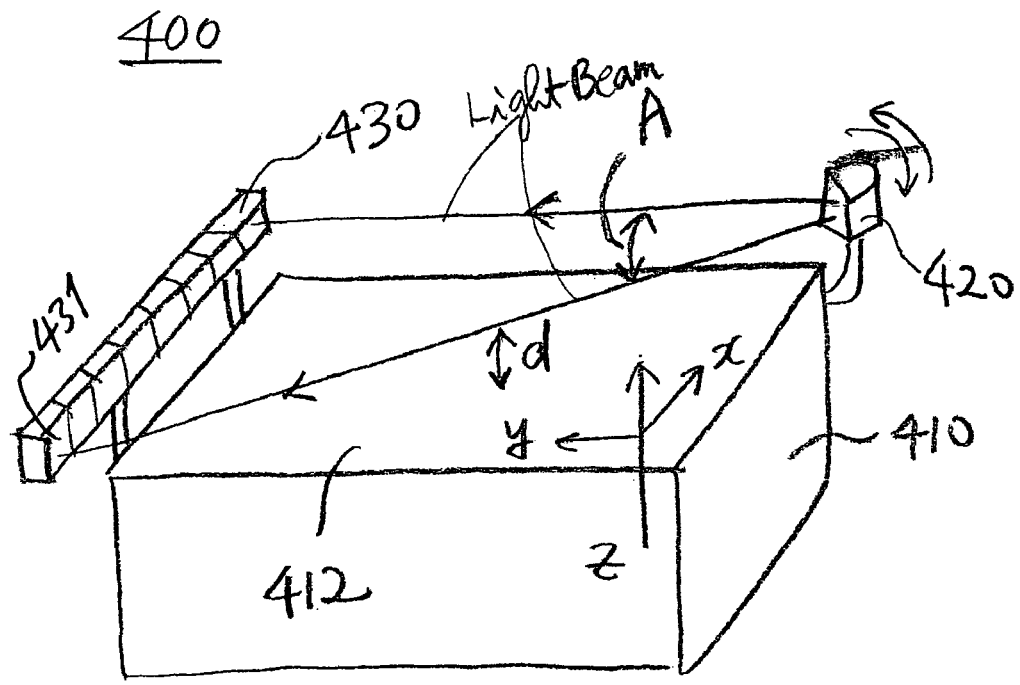
FIG. 15 illustrates a perspective view of another embodiment of the present invention.
Figure 19:
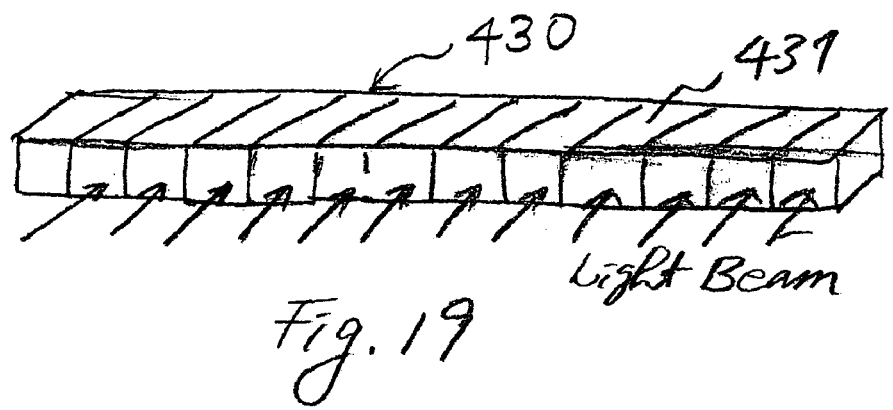
FIGS. 19 and 20 illustrate embodiments of a light source and detector which can be used in the present invention.
Figure 20:
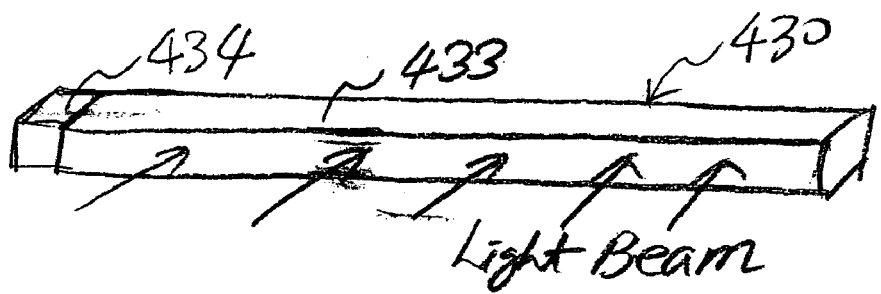

FIG. 15 schematically depicts another embodiment of the apparatus of the invention. In this embodiment, the physical components are almost the same as in the previous embodiment of FIGS. 13 and 14, except for the shape of the light detector. As shown in FIG. 15, the light detector 430 takes an elongated shape formed parallel to the camera surface 412. The light source 420 is designed to oscillate or rotate such that the light beam can sweep over the camera surface 12 as indicated by an arrow A and be detected by the elongated light detector 430 during the oscillation or rotation of the source 420, thereby more efficiently detect approaching the patient body. In this case, the light detector 430 can be much longer than is shown in FIG. 15 such that the sweeping light beam can cover even larger area of the camera surface 412. FIGS. 19 and 20 schematically illustrate two examples of the elongated light detector 430. As shown in FIG. 19, the light detector 430 comprises a plurality of photo-sensors 431 arranged parallel to the camera surface 412. During the sweeping of the light, the photo-sensors 431 detect the light beam in succession, and also sense any interruption or disturbance of the beam by a patient's body when and where it occurs. Alternatively, as depicted in FIG. 20, the elongated light detector 430 can comprise an optical bar 433, for example, a sheet of Plexiglas™, for receiving the sweeping light beam, and a photo-sensor 434 disposed at one end of the optical bar 433 for detecting the light received therein. The photo-sensor 434 can be disposed at any position where it can detect the light received in the optical bar 433 (the sheet of Plexiglas™). In the embodiment of FIG. 20, the received light beam will be reflected and dispersed repeatedly therein and brighten the inside of the sheet 433 such that it can be detected or sensed by the photo-sensor 434.

Figure 16:
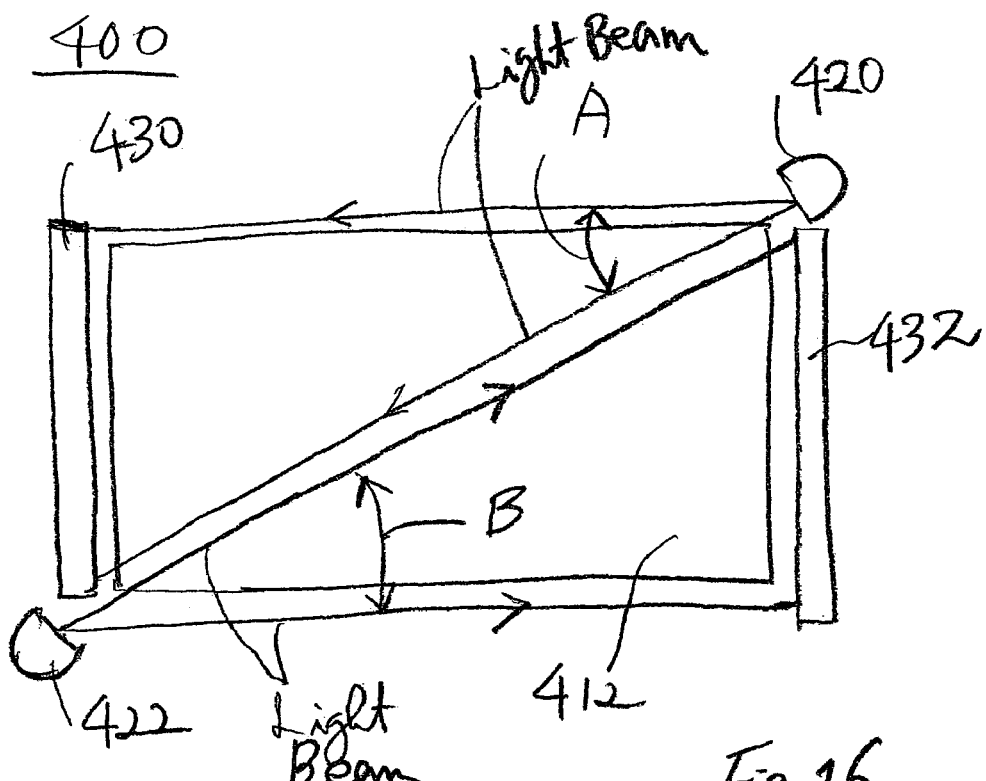
FIG. 16 schematically shows an alternative form of FIG. 15.

FIG. 16 schematically illustrates another embodiment similar to the previous one of FIG. 15. In this embodiment, the apparatus 400 further comprises an additional light source 422 and an additional elongated light detector 432. Similar to FIG. 15, the additional light source 422 is also adapted to oscillate or rotate in such a manner that a light beam emitted therefrom can sweep over the camera surface 412 as indicated by an arrow B and be detected by the additional elongated light detector 432 during the sweeping of the light. The additional light detector 432 can also take the form as depicted in FIG. 19 or 20. Due to the irregular profile of the approaching patient's body, an interruption or disturbance in the light beam can occur anywhere over the camera surface 412. Therefore, with the apparatus 400 of this embodiment, the light beam can sweep substantially the whole area of the camera surface 412 such that it can more efficiently detect the interruption or disturbance of the light beam wherever it occurs over the camera surface, thereby to more effectively control the relative distance between the patient's body and the camera head 410.

In the embodiment of FIG. 15, the light source 420 can take an elongated shape, instead of the oscillating or rotating thereof. That is, the elongated light source 420 can emit, for example, a sheet-like light beam parallel to the camera surface 412 while maintaining a distance d therefrom although not shown in FIG. 15. Alternatively, the elongated light source can comprise a plurality of light emitters arranged parallel to the camera surface 412, each of which corresponds to each respective photo-sensor of FIG. 19. Thus, each light beam emitted by each light emitter will be detected by each respective photo-sensor 431 of the light detector 430. The light emitter may include a laser. Therefore, as in the previous embodiment of FIG. 16, the sheet-like light beam or the multiple light beams can cover substantially the whole area of the camera surface 412 such that the apparatus can more efficiently and effectively control the relative distance d between the patient's body and the camera head 410.

Figure 17:
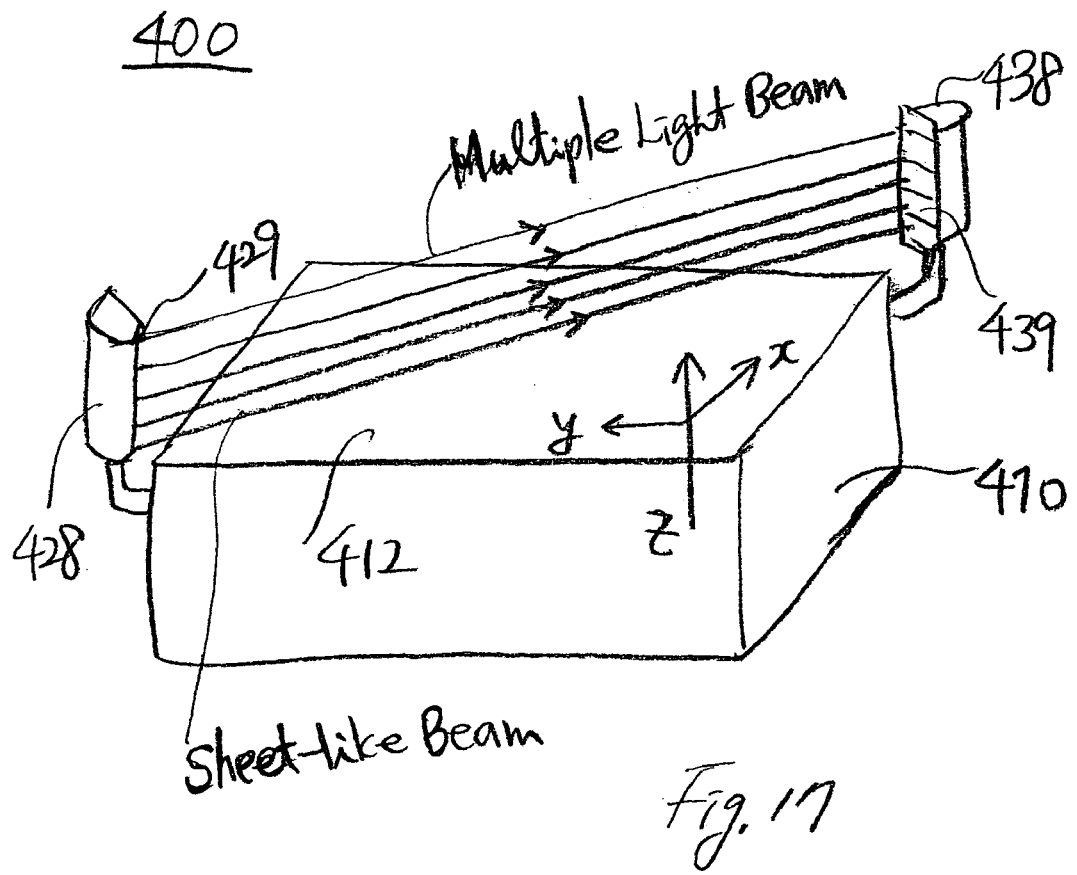
FIG. 17 depicts a perspective view of yet another embodiment of the present invention.
Figure 18:
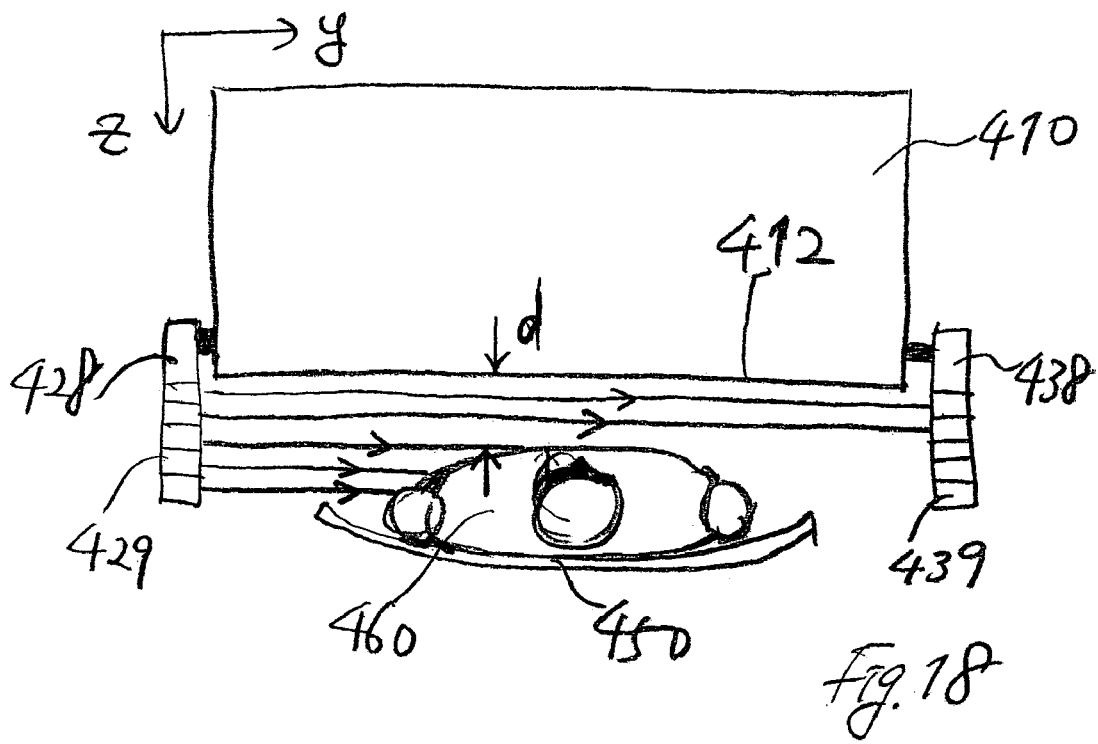
FIG. 18 shows a frontal view of FIG. 17.

FIG. 17 schematically depicts yet another embodiment of the apparatus of the invention, which comprises an elongated light source 428 and an elongated light detector 438, both being arranged perpendicular to the camera surface 412. In this embodiment, the light source 428 is adapted to emit a sheet-like beam substantially perpendicular to the camera surface 412 and the light detector 438 is adapted to detect the sheet-like beam at multiple heights over the camera surface as shown in FIG. 17. The elongated light detector can take a form similar to that of FIG. 19, i.e., comprise a plurality of photo-sensors 439 arranged perpendicular to the camera surface 412. The photo-sensor may include a charge coupled device (CCD) or a photodiode. Each photo-sensor 439 can correspond to each respective height. Therefore, the distance of a patient from the camera surface can be more efficiently and flexibly controlled as shown in FIG. 18, which is a frontal view of FIG. 17. Also, a certain distance d can be pre-set programmably in a camera control electronic (not shown).

Further, the light source 428 can be adapted to emit multiple light beams arranged perpendicular to the camera surface, instead of the sheet-like beam. For example, the elongated light source 428 can comprise a plurality of light emitters 429 as depicted in FIGS. 17 and 18, where each light emitter 429 corresponds to each respective photo-sensor 439 in the same operational mode as noted above. The light emitter may include a laser.

Figure 21:
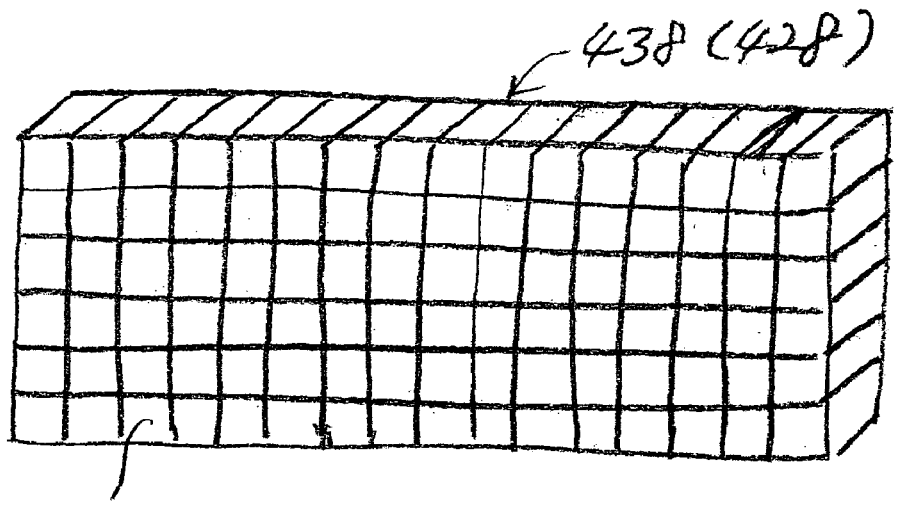
FIG. 21 illustrates another embodiment of a light source and detector which can be used in the present invention.

In the embodiment illustrated in FIGS. 17 and 18, the light source 428 can oscillate or rotate such that the sheet-like beam or the multiple light beams sweep over the camera surface 412, in substantially the same operational mode as noted above in conjunction with FIG. 15. In this case, the light detector 438 comprises a plurality of photo-sensors 439 arranged in rows and columns as illustrated in FIG. 21. Alternatively, the light detector 438 can comprise multiple layers of the elongated light detectors 430 depicted in FIG. 19 or 20.

Further, an additional oscillating light source and an additional light detector can be provided and operated in substantially the same mode as in FIG. 16. That is, the additional light source is adapted to emit a sheet-like beam or multiple light beams arranged perpendicular to the camera surface and to oscillate or rotate in such a manner that the additional light beam can sweep over the camera surface. The additional light detector can comprise a plurality of photo-sensor arranged in rows and columns which can detect the additional light beam during the oscillation of the additional light source. Therefore, the light beams emitted by the two light sources can sweep substantially the whole area of the camera surface, as illustrated in FIG. 16.

Furthermore, the light source 428 and detector 438 both can take a form illustrated in FIG. 21. That is, the light source 428 comprises a plurality of light emitters arranged in rows and columns and the light detector 438 a plurality of photo-sensors arranged in rows and columns. Each light emitter corresponds to each respective photo-sensor. As is apparently understood to those skilled in the art, the light source and detector, or every light emitter and photo-sensor thereof can be communicatively and operatively connected to a camera control circuitry or a separate control unit. Therefore, the apparatus of this embodiment can detect the profile of the patient's body while taking pictures such that it can more efficiently and effectively control, in real time, the distance of the patient's body from the camera surface, especially when carrying out a whole body scanning.

For a whole or partial body scan, the camera head 410 moves along the X-axis, i.e., in the longitudinal direction of the patient, as discussed above in conjunction with FIGS. 1–12. The apparatus of the invention will automatically adjust the camera head at an optimum distance from the patient during scanning the body according to the profile of the patient. After scanning the body, the camera path along the patient profile can be memorized in a camera processing computer or unit. This data can be advantageously used for a subsequent can or for a multiple scanning study.

In some instances, the camera head is required to rotate around a patient's body to take different views thereof. The apparatus of the present invention will provide a good controllability in maintaining an optimum distance of the patient body from the camera surface, for example, in combination with the structure and operation of the camera system as discussed above in connection with FIGS. 1 to 12.

While the present invention has been described with reference to several specific embodiments, the description is of illustrative of the invention and is not to be construed as limiting the invention. Various modifications and variations may occur to those skilled in the art without departing from the true spirits and scope of the invention as defined by the appended claims.

What is claimed is:

1. A medical imaging system comprising:
    a camera head including a camera surface, said camera surface defining a field of view where a patient's body is to be placed;
    a mechanism for rotating said camera head around said patient's body in a first plane and moving said camera head in a second plane substantially parallel to said first plane;
    a light source being adapted to emit a light beam which travels over and substantially parallel to said camera surface, said light source being mounted on said camera head;
    a light detector being adapted to detect said light beam emitted from said light source at least at multiple heights over said camera surface, said light detector being mounted on said camera head and being spatially separated from said light source such that a space between said light source and said light detector is sufficient to place said patient's body therein;
    a module for analysing characteristics detected by said light detector and measuring a distance between said patient's body and said camera surface; and
    a controller for controlling said mechanism based on an output of said module to adjust a relative distance between said patient's body and said camera surface.

2. A system according to claim 1, wherein said controller is adapted to prevent said camera head and said patient's body from approaching each other based on interruption or disturbance in said light beam.

3. A system according to claim 2, wherein said controller is adapted to adjust said predetermined distance.

4. A system according to claim 1, wherein said light source includes a laser.

5. A system according to claim 1, wherein said light detector includes a charge coupled device (CCD) or a photodiode.

6. A system according to claim 1, wherein said light source is adapted to oscillate in such a manner that said light beam sweeps over the camera surface and said light detector is adapted to detect the light beam at said multiple heights or at said multiple heights and at multiple points substantially parallel to the camera surface.

7. A system according to claim 6, wherein said light detector comprises a plurality of photo-sensors arranged perpendicular to the camera surface.

8. A system according to claim 6, wherein said light detector comprises an optical bar for receiving said sweeping light beam at said multiple heights and a photo-sensor for detecting said received light beam.

9. A system according to claim 6, further comprising:
    an additional light source being adapted to oscillate in such a manner that a light beam emitted by said additional light source sweeps over the camera surface, and
    an additional light detector being adapted to detect said additional light beam at multiple points to the camera surface,
    wherein the light beams emitted by said two light sources are capable of sweeping substantially the whole area of the camera surface.

10. A system according to claim 1, wherein said light source is adapted to emit a sheet-like light beam which travels substantially parallel to said camera surface and covers a plane substantially perpendicular to said camera surface.

11. A system according to claim 10, wherein said light detector comprises a plurality of photo-sensors arranged perpendicular to said camera surface.

12. A system according to claim 10, wherein said light detector comprises an optical bar for receiving said light beam at said multiple heights, and a photo-sensor for detecting said received light beam.

13. A system according to claim 10, wherein said light detector has an elongated shape, and is mounted on said camera head so as to extend substantially perpendicular to said camera surface.

14. A system according to claim 10, wherein said light source is adapted to oscillate in such a manner that said sheet-like light beam sweeps over said camera surface, and said light detector comprises a plurality of photo-sensors arranged in rows and columns which detect said sweeping sheet-like light beam.

15. A system according to claim 14, further comprising:
an additional light source being adapted to emit a sheet-like light beam which travels substantially parallel to said camera surface and covers a plane substantially perpendicular to said camera surface, said additional light source being adapted to oscillate in such a manner that said sheet-like light beam emitted by said additional light source sweeps over said camera surface, and
an additional light detector comprising a plurality of photo-sensors arranged in rows and columns which detect said additional sheet-like light beam during the sweeping thereof,
wherein said light beams emitted by said light source and said additional light source are capable of sweeping substantially the whole area of said camera surface.

16. A system according to claim 1, wherein said light source includes a plurality of light emitters arranged substantially perpendicular to said camera surface, each of said light emitter is adapted to emit a light beam substantially parallel to said camera surface, and each of said multiple heights corresponds to the height of a respective light emitter.

17. A system according to claim 16, wherein said light detector comprises a plurality of photo-sensors arranged perpendicular to said camera surface, each of which corresponds to a respective light emitter.

18. A system according to claim 16, wherein said light source is adapted to oscillate in such a manner that a light beam emitted by each of said light emitters sweeps over said camera surface, and said light detector comprises a plurality of photo-sensors arranged in rows and columns.

19. A system according to claim 18, further comprising:
an additional light source comprising a plurality of light emitters arranged substantially perpendicular to said camera surface, each of said light emitters being adapted to emit a light beam substantially parallel to said camera surface, said additional light source being adapted to oscillate in such a manner that a light beam emitted by each of said light beams sweeps over said camera surface, and
an additional light detector comprising a plurality of photo-sensors arranged in rows and columns,
wherein said light beams emitted by said light source and said additional light source are capable of sweeping substantially the whole area of said camera surface.

20. A system according to claim 1, wherein said light source comprises a plurality of light emitters arranged in rows and columns, and said light detector comprises a plurality of photo-sensors arranged in rows and columns, each of said light emitters corresponding to a respective photo-sensor.

21. A system according to claim 1, wherein said light beam is capable of sweeping substantially the whole area of the camera surface.

22. A system according to claim 21, wherein said camera head is adapted to scan said patient's body, and said apparatus is adapted to keep adjusting said relative distance between said patient's body and said camera surface at a predetermined value during said scanning.

23. A system according to claim 22, further comprising means for memorizing a path of said camera head according to a profile of said patient after said body scanning.

24. A system according to claim 21, wherein said light source includes a laser.

25. A system according to claim 21, wherein said light detector includes a charge coupled device (CCD) and a photodiode.

26. A system according to claim 1, further comprising a profile detector for detecting a profile of said patient based on said characteristics detected by said light detector.

27. A system according to claim 26, further comprising a memory for storing said profile, said controller being capable of adjusting said relative distance based on said profile stored in said memory.

28. A system according to claim 1, wherein said mechanism includes:
(i) an annular support for defining an orifice around said patient's body, and being rotatable around said patient's body,
(ii) an elongate support for supporting said camera head and being rotatable with said annular support, and
(iii) a guide for controlling said elongate support such that said camera head is moved substantially parallel to a plane defined by said orifice.

29. A method of positioning a camera head in a medical system, said camera head having a camera surface, said camera surface defining a field of view where a patient's body is to be placed, said method comprising the steps of:
at a light source, projecting a light beam in such a manner that said light beam travels over and substantially parallel to said camera surface, said light source being mounted on said camera head;
at a light detector, detecting said light beam at least at multiple heights over said camera surface, said light detector being mounted on said camera head and being spatially separated from said light source such that a space between said light source and said light detector is sufficient to place said patient's body therein;
at a controller, analysing characteristics in said detected light beam, including measuring a distance between said patient's body and said camera surface, said light beam being interrupted or disturbed by said patient's body placed in said field of view; and
based on the analysis, moving said camera head or the patient's body to adjust a relative distance between said camera surface and said patient's body, said camera head being rotatable around said patient's body in a rotation plane and movable substantially parallel to said rotation plane.

30. A method according to claim 29, further comprising steps of:
scanning said patient's body with said camera head; and
adjusting said relative distance between said patient's body and said camera surface during said scanning.

31. A method according to claim 30, further comprising steps of:
- detecting a profile of said patient based on said analysis; and
- memorizing a path of said camera head according to said profile of said patient after said step of body scanning.

32. A method according to claim 29, wherein said projecting step includes the step of emitting a plurality of light beams which travel substantially parallel to said camera surface and cover a plane substantially perpendicular to said camera surface.

33. A method according to claim 32, further comprising the steps of:
- at an additional light source, emitting a sheet-like light beam which travels substantially parallel to said camera surface and covers a plane substantially perpendicular to said camera surface;
- moving said additional light source such that said sheet-like light beam sweeps over said camera surface;
- at a plurality of photo-sensors arranged in rows and columns, detecting said sweeping sheet-like light beam,
- whereby said light beams emitted by said light source and said additional light source are capable of sweeping substantially the whole area of said camera surface.

34. A method according to claim 29, wherein said projecting step includes the step of emitting a sheet-like light beam which travels substantially parallel to said camera surface and covers a plane substantially perpendicular to said camera surface.

35. A method according to claim 29, wherein said projecting step includes the step of moving said light source such that said light beam sweeps over said camera surface.

36. A method according to claim 35, wherein said detecting step includes the step of detecting said sweeping light beam at said multiple heights or at said multiple heights and at multiple points parallel to said camera surface.

37. A method according to claim 35, further comprising the steps of:
- at an additional light source, emitting a plurality of additional light beams which travel substantially parallel to said camera surface and cover a plane substantially perpendicular to said camera surface;
- moving said additional light source such that said additional light beams sweep over said camera surface;
- at a plurality of photo-sensors arranged in rows and columns, detecting said sweeping light beams,
- whereby said light beams emitted by said light source and said additional light source are capable of sweeping substantially the whole area of said camera surface.

38. A method according to claim 29, wherein said medical system includes (i) an annular support for defining an orifice around said patient's body, and being rotatable around said patient's body, and (ii) an elongate support for supporting said camera head and being rotatable with said annular support, and
- said moving step includes the step of controlling said elongate support such that said camera head is moved substantially parallel to a plane defined by said orifice.

39. An apparatus for controlling a relative distance between a patient and a camera head, said camera head being adapted to produce image of said patient and defining a field of view, said apparatus comprising:
- a light source including a plurality of light emitters arranged substantially perpendicular to said camera surface and being adapted to emit a plurality of light beams substantially parallel to said camera surface, said light source being mounted on said camera head;
- a light detector being adapted to detect said light beams at least at multiple heights over said camera surface, said light detector being mounted on said camera head and being spatially separated from said light source such that a space between said light source and said light detector is sufficient to place said patient's body therein;
- a module for analysing interruption or disturbance in said light beams and measuring a distance between said patient's body and said camera surface; and
- a mechanism for adjusting said relative distance between said patient and said camera surface based on an output of said module.

40. An apparatus according to claim 39, wherein said light detector includes a plurality of photo-sensors arranged substantially perpendicular to said camera surface.

41. An apparatus according to claim 39, wherein said light detector has an elongated shape, and is mounted on said camera head so as to extend substantially perpendicular to said camera surface.

42. An apparatus according to claim 39, wherein said light source is oscillated such that said light beam sweeps over said camera surface.

43. An apparatus according to claim 42, wherein said light detector includes an optical bar for receiving said sweeping light beam, and a photo-sensor for detecting said received light beam.

44. An apparatus according to claim 39, wherein said light source includes a plurality of light emitters arranged in rows and columns, and said light detector is adapted to detect light beams emitted by said light emitters.

45. An apparatus according to claim 39, further comprising:
- an additional light source being adapted to emit a set of light beams or a sheet-like light beam such that said set of light beams or said sheet-like light beam travels substantially parallel to said camera surface and covers a plane substantially perpendicular to said camera surface; and
- a plurality of photo-sensors arranged in rows and columns arranged for said additional light source,
- wherein said light beams emitted by said light source and said additional light source are capable of sweeping substantially the whole area of said camera surface.

46. An apparatus according to claim 39, wherein said module includes a detection module for detecting a profile of said patient's body based on said interruption or disturbance.

47. An apparatus for controlling a relative distance between a patient and a camera head, said camera head being adapted for producing image of said patient and defining a field of view, said apparatus comprising:
- a light source being adapted to emit a sheet-like light beam which travels substantially parallel to said camera surface and covers a plane substantially perpendicular to said camera surface, said light source being mounted on said camera head;
- a light detector being adapted to detect said sheet-like light beam at least at multiple heights over said camera surface, said light detector being mounted on said camera head and being spatially separated from said light source such that a space between said light source and said light detector is sufficient to place said patient's body therein;

a module for analysing interruption or disturbance in said sheet-like light beam and measuring a distance between said patient's body and said camera surface; and a mechanism for adjusting said relative distance between said patient and said camera surface based on an output of said module.

48. An apparatus according to claim 47, wherein said light detector includes a plurality of photo-sensors arranged substantially perpendicular to said camera surface.

49. An apparatus according to claim 47, wherein said light detector has an elongated shape, and is mounted on said camera head so as to extend substantially perpendicular to said camera surface.

50. An apparatus according to claim 47, wherein said light source is oscillated such that said sheet-like light beam sweeps over said camera surface.

51. An apparatus according to claim 50, wherein said light detector includes an optical bar for receiving said sweeping light beam, and a photo-sensor for detecting said received light beam.

52. An apparatus according to claim 47, wherein said light source includes a plurality of light emitters arranged in rows and columns, and said light detector is adapted to detect light beams emitted by said light emitters.

53. An apparatus according to claim 47, further comprising:

an additional light source being adapted to emit a set of light beams or an additional sheet-like light beam such that said set of light beams or said additional sheet-like light beam travels substantially parallel to said camera surface and cover a plane substantially perpendicular to said camera surface; and a plurality of photo-sensors arranged in rows and columns arranged for said additional light source, wherein said light beams emitted by said light source and said additional light source are capable of sweeping substantially the whole area of said camera surface.

54. A method according to claim 47, wherein said module includes a detection module for detecting a profile of said patient's body based on said interruption or disturbance.

* * * * *